(12) United States Patent
Patel

(10) Patent No.: US 11,664,124 B2
(45) Date of Patent: *May 30, 2023

(54) SYSTEM FOR REMOTE MEDICAL CARE

(71) Applicant: Kevin Patel, Dallas, TX (US)

(72) Inventor: Kevin Patel, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/705,594

(22) Filed: Mar. 28, 2022

(65) Prior Publication Data

US 2022/0215954 A1    Jul. 7, 2022

Related U.S. Application Data

(63) Continuation of application No. 17/346,066, filed on Jun. 11, 2021, now Pat. No. 11,289,195.

(60) Provisional application No. 63/151,757, filed on Feb. 21, 2021, provisional application No. 63/113,895, filed on Nov. 15, 2020, provisional application No. 63/063,320, filed on Aug. 9, 2020.

(51) Int. Cl.
*G08B 21/00* (2006.01)
*G16H 40/67* (2018.01)
*A61B 50/33* (2016.01)
*G16H 80/00* (2018.01)
*A61B 50/00* (2016.01)

(52) U.S. Cl.
CPC ............ *G16H 40/67* (2018.01); *A61B 50/33* (2016.02); *G16H 80/00* (2018.01); *A61B 2050/005* (2016.02)

(58) Field of Classification Search
CPC ........ G16H 40/67; G16H 80/00; A61B 50/33; A61B 2050/005
See application file for complete search history.

(56) References Cited

U.S. PATENT DOCUMENTS

| | | | | |
|---|---|---|---|---|
| 3,962,805 | A * | 6/1976 | Hamu | D06C 3/08 101/127.1 |
| 5,537,290 | A * | 7/1996 | Brown | F16M 11/2092 248/458 |
| 5,802,483 | A * | 9/1998 | Morris | H04L 9/40 455/553.1 |
| 6,076,786 | A * | 6/2000 | Meyer | G06F 1/162 248/920 |
| 9,473,606 | B1 * | 10/2016 | Sumida | H04M 1/04 |
| 2001/0016696 | A1 * | 8/2001 | Bystrom | A61N 1/3987 601/41 |

(Continued)

OTHER PUBLICATIONS

Kwon et al., Application of Telemedicine System to Prehospital Medical Control (Year: 2015).*

(Continued)

*Primary Examiner* — Quang Pham
(74) *Attorney, Agent, or Firm* — Scale LLP

(57) ABSTRACT

Systems and methods for remote medical care are described. In some embodiments, a system may include a case that houses one or more of a display, a microphone, a camera, a plurality of medical devices, and a computing device. In some embodiments, the computing device may be configured to communicate with one or more of the display, the microphone, the camera, and the plurality of medical devices. In some embodiments, the display may be coupled to a lid of the case by a support arm that is pivotable relative to the lid to allow a position of the display to be adjusted.

19 Claims, 10 Drawing Sheets

(56) References Cited

U.S. PATENT DOCUMENTS

| | | | | |
|---|---|---|---|---|
| 2002/0186243 | A1* | 12/2002 | Ellis | G16H 40/67 |
| | | | | 348/E7.078 |
| 2003/0038047 | A1* | 2/2003 | Sleva | A61B 50/31 |
| | | | | 206/370 |
| 2007/0135866 | A1* | 6/2007 | Baker | A61B 5/1113 |
| | | | | 600/407 |
| 2008/0216125 | A1* | 9/2008 | Li | G06F 3/1446 |
| | | | | 375/E7.076 |
| 2010/0320341 | A1* | 12/2010 | Baumann | F16B 47/006 |
| | | | | 248/299.1 |
| 2011/0105898 | A1* | 5/2011 | Guthart | A61B 1/04 |
| | | | | 600/109 |
| 2012/0026119 | A1* | 2/2012 | Judy | G16H 40/67 |
| | | | | 345/173 |
| 2012/0106528 | A1* | 5/2012 | Estevez | H04W 88/06 |
| | | | | 370/338 |
| 2012/0281970 | A1* | 11/2012 | Garibaldi | H04N 21/2665 |
| | | | | 348/E7.083 |
| 2013/0109928 | A1* | 5/2013 | Menzel | G16H 40/63 |
| | | | | 600/301 |
| 2013/0134843 | A1* | 5/2013 | Molewyk | A47F 10/00 |
| | | | | 312/198 |
| 2014/0018779 | A1* | 1/2014 | Worrell | A61B 90/00 |
| | | | | 606/1 |
| 2014/0187284 | A1* | 7/2014 | Sanchez | H04B 7/0814 |
| | | | | 455/550.1 |
| 2015/0068942 | A1* | 3/2015 | Gerstner | A61B 50/33 |
| | | | | 206/370 |
| 2015/0173670 | A1* | 6/2015 | Simon | A61B 5/746 |
| | | | | 702/150 |
| 2015/0302417 | A1* | 10/2015 | DeCelles | G06Q 30/016 |
| | | | | 705/304 |
| 2016/0332589 | A1* | 11/2016 | Van Wiemeersch | |
| | | | | G07C 5/0816 |
| 2016/0371443 | A1* | 12/2016 | Kudo | G16H 40/67 |
| 2017/0024537 | A1* | 1/2017 | Ferlito | G16H 40/67 |
| 2018/0146645 | A1* | 5/2018 | Arbel | A01K 11/006 |
| 2018/0226158 | A1* | 8/2018 | Fish | A61B 5/0022 |
| 2018/0236114 | A1* | 8/2018 | Davis | A61L 2/24 |
| 2018/0302937 | A1* | 10/2018 | Nieminen | H04W 4/33 |
| 2019/0086022 | A1* | 3/2019 | Anderson | F16M 11/2014 |
| 2019/0097831 | A1* | 3/2019 | Kim | H04W 4/14 |
| 2019/0234132 | A1* | 8/2019 | Barke | G05B 19/41865 |
| 2019/0274451 | A1* | 9/2019 | Twohy | A47F 3/04 |
| 2020/0147427 | A1* | 5/2020 | Atkinson | H02J 7/0042 |
| 2020/0236931 | A1* | 7/2020 | Trainor | A01N 47/44 |
| 2021/0157463 | A1* | 5/2021 | Gerder-Kallisch | G06F 3/0484 |
| 2021/0239262 | A1* | 8/2021 | Lim | F16M 11/2092 |
| 2022/0082206 | A1* | 3/2022 | Walker | F16M 11/2092 |

OTHER PUBLICATIONS

VSee Telemedicine for Syrian Refugees in Dohuk Iraq Kurdistan (Year: 2014).*

Wayne Caswell, TeleHealth The Doctor Will See You Now Remotely (Year: 2014).*

Telehealth Solutions, Pediatrics Specialty Medium Rugged Telemedicine Kit (Year: 2019).*

* cited by examiner

SYSTEM FOR REMOTE MEDICAL CARE

CROSS-REFERENCE TO RELATED APPLICATIONS

This application is a continuation of U.S. patent application Ser. No. 17/346,066, filed Jun. 11, 2021, which claims the benefit of U.S. provisional patent application No. 63/151,757, filed Feb. 21, 2021, U.S. provisional patent application No. 63/113,895, filed Nov. 15, 2020, and U.S. provisional patent application No. 63/063,320 filed Aug. 4, 2020, each of which is hereby incorporated by reference herein in its entirety.

FIELD OF THE DISCLOSURE

This disclosure relates to systems and methods for remote medical care. Specifically, this disclosure relates to a medical case configured to enable telehealth appointments, including in remote locations with limited internet service, in-home care, early hospital releases, and field triage.

BACKGROUND

Millions of patients live in remote and rural areas with limited internet services. Currently, thousands of dollars are spent to transport these patients to hospitals where they can be seen by doctors and then back home to their communities. This practice is expensive and undesirable for the patient, who must spend hours traveling.

There are a number of technical challenges that have prevented the practice of long-distance travel for in-person visits from being replaced with telehealth appointments. For example, many rural communities lack reliable high-speed internet service. Without high-speed internet, a stable video feed cannot be established to allow a doctor to effectively evaluate a patient. Further, to further reduce cost and burden, the patent must be able to self-administer the appointment. That is, if a technician must travel out to the patient to set up the telehealth appointment, much of the cost savings and efficiency of the telehealth appointment is lost.

Accordingly, there is a need for systems and methods that can enable telehealth appointments in remote areas with limited internet service. Further, there is a need for systems and methods that will allow these telehealth appointments to be easily and reliably self-administered by patients.

SUMMARY

The following description presents a simplified summary in order to provide a basic understanding of some aspects described herein. This summary is not an extensive overview of the claimed subject matter. It is intended to neither identify key or critical elements of the claimed subject matter nor delineate the scope thereof.

In some embodiments, a telehealth system may be provided. The telehealth system may include a case housing one or more of a display, a microphone, a camera, a plurality of medical devices, a plurality of antennas, a plurality of access credentials, and a computing device. In some embodiments, the system may be configured to obtain, using a first medical device of the plurality of medical devices, patient data indicating a health parameter of a patient. The system may be configured to transmit the patient data to the computing device. The system may be configured to obtain, using the microphone, audio data, and to obtain, using the camera, video data. In some embodiments, the system may be configured to generate a plurality of data packets which may collectively comprising information related to the patient data, the audio data, and the video data.

In some embodiments, the system may be configured to establish, using at least in part the plurality of access credentials, communications links with a plurality of network nodes, the plurality of nodes comprising a first node and a second node, and transmit, using a first antenna of the plurality of antennas, a first set of data packets of the plurality of data packets to the first node. While transmitting the first set of data packets to the first node using the first antenna, the system may transmit, using a second antenna of the plurality of antennas, a second set of data packets of the plurality of data packets to the second node. In some embodiments, the system may detect an interruption in the link to the first node, and as a result of detecting the interruption, transmit a third set of data packets to the second node, wherein the third set of data packets would have been sent to the first node in the absence of the detected interruption.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

As used herein, the term "or" includes both conjunctive and disjunctive cases, and should be interpreted as "and/or" unless otherwise stated.

Figure 1:
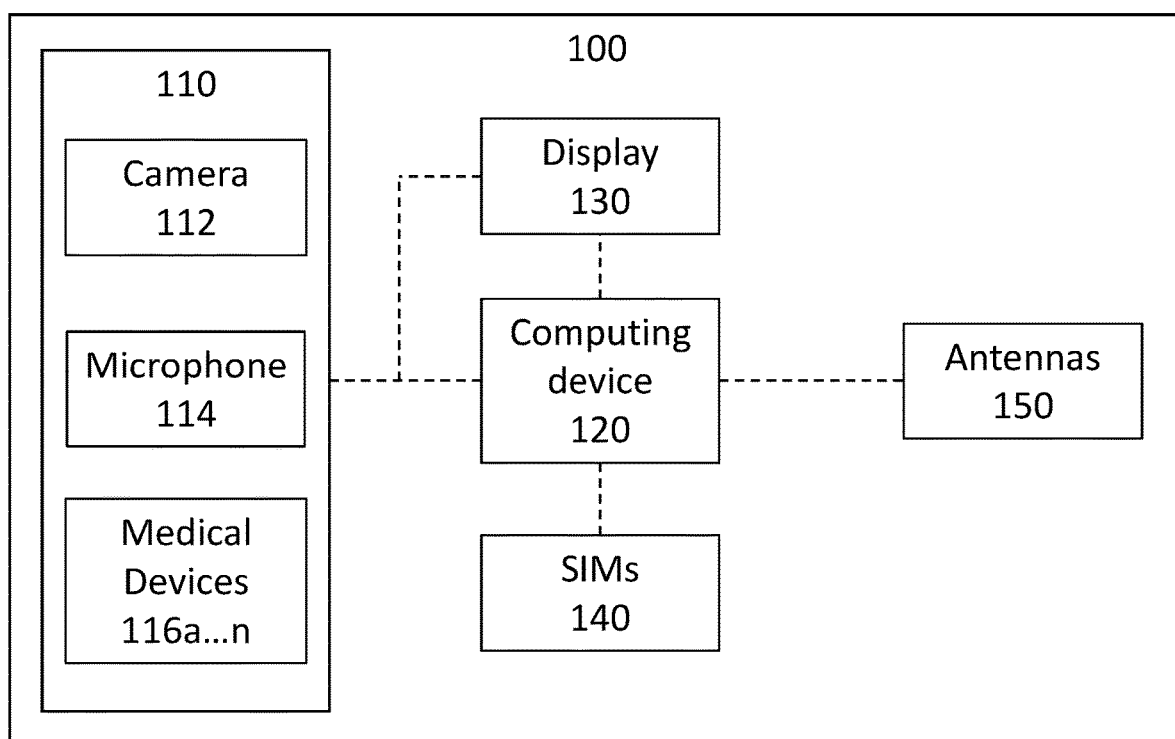
FIG. 1 shows an exemplary system 100 for enabling remote medical care.

FIG. 1 shows an exemplary system 100 for enabling remote medical care. The system may include a plurality of data capturing devices 110. For example, the system may include one or more cameras 112, one or more microphones, and a plurality of medical devices 116a-116n. In some embodiments, the medical devices may include one, some, or all of a stethoscope, a pulse-oximeter, a blood pressure cuff, a temperature sensors, a blood glucose sensor, a hematocrit sensor, an otoscope, a cold storage chamber, wound care bandages, medications, IV bags, biological supportive fluids, and/or tubes for collecting samples (e.g., saliva, blood, tissue).

In some embodiments, data obtained by the data capturing devices 110 may be transmitted, in whole or in part, to a doctor at a remote location. For example, a patient may engage in a videoconference with the doctor while the patient (or a technician) uses the medical devices to obtain patient data.

The data capturing devices 110 may transmit data to a computing device 120, which may include one or more processors. The computing device 120 may be operatively coupled to one or more antennas for wireless communications. For example, the computing device 120 may communicate via Bluetooth, WiFi, satellite antennas, cellular, LTE, 5G, sub 6 GHz networks, mmWave, or any other suitable wireless or wired communication technology. The computing device 120 may be a single device, or it may include multiple devices operatively connected to one-another. In some embodiments, one, some, or all of the medical devices 116a-116n may be establish wireless communications with the computing device so that the patient data collected by the respective medical devices can be wirelessly transmitted to the computing device. The wireless communications between the medical devices 116a-116n and the computing device may be direct or indirect. For example, in some embodiments, the medical devices 116a-116n may communicate directly with display 130, which may in turn communicate with computing device 120. In some embodiments, the computing device 120 and/or display 130 may establish wireless communication channels with multiple of the medical devices 116 to receive multiple types of patient data simultaneously. Similarly, the one or more cameras 112 and microphones 114 may also establish wireless communications with the computing device and/or display 130. In this manner, video and audio data may be captured and transmitted to the computing device.

In some embodiments, the data capturing devices 110 may also transmit data to the display 130. It may be desirable for the patient to see indications of some or all of the patient data. For example, a pulse oximeter may wirelessly communicate pulse or oxygenation levels to the display, so that an indication of the patient's pulse or oxygenation may be displayed to the patient. In some embodiments, data may be transmitted directly from the data capturing devices to the display. In other embodiments, data may be transmitted first from the data capturing devices to the computing device, and from the computing device to the display. The latter case may be advantageous where one or more of the medical devices are not enabled to maintain wireless communications with multiple devices simultaneously, or where it is desirable to process the patient data at the computing device before it is transmitted to the display. In some embodiments, data may be sent first to the display 130, which may then relay the data to the computing device. Communicating patient data to both the display 130 and the computing device 120 it may advantageously allow for both the patient and the doctor to see the same data.

In some embodiments, the camera and the microphone may be associated with the display. For example, a display may be a tablet device that includes a microphone, one or more cameras, one or more speakers. In other embodiments, the microphone, cameras, and/or speakers may be separate from the display. The display may also include one or more processors, memory, and antennas. The antennas of the display may be used to enable wireless communication with the computing device 120 and medical devices 116. The display may also include antennas that can be used to transmit and receive information with nodes of a telecommunications network. While the system may advantageously include high-powered antennas 150 that may be primarily used for transmitting and receiving data in remote locations, antennas in the display 130 may optionally be used in areas with stronger cell signals.

In some embodiments, the system 100 may include a access credentials. In some embodiments, one or more of the access credentials may be subscriber identification modules (SIMs). The system may use the access credentials to establish telecommunications links with a plurality of network nodes, which may optionally be associated with different network providers. The network nodes may be nodes of any suitable wireless communication network, including, for example, cellular networks or satellite networks. The computing device 120 may access subscriber information of the access credentials to establish these telecommunication links.

The system 100 may include a plurality of antennas 150. The antennas may be used to transmit and receive data with multiple network nodes simultaneously. For example, the plurality of antennas 150 may include a first antenna that may communicate with a first node and a second antenna that may communicate with a second node. Any number of antennas may be provided to communicate simultaneously with any number of network nodes. As described in greater detail below with respect to FIG. 2, data collected by the data capture devices 100 may be transmitted to the computing device 120, through antennas 150 to telecommunication nodes, and then through a wide area network (WAN) to a computing device used by a doctor. The doctor may conduct a videoconference with the patient. The doctor's device may also include cameras and microphones, which may transmit audio and video data through the WAN, network nodes, and back to the computing device 120 through the antennas 150. The audio and video data may then be played for the patient. For example, this data may be transmitted from the computing device to the display, where it may be played.

In some embodiments, wireless communications may be established between the computing device and one, some, or all of (i) the medical devices 116, (ii) the display 130, and (iii) one or more telecommunications nodes. For example, patient data may be transmitted, using a first wireless communication protocol, from a first medical device 116a, directly or indirectly, to the computing device 120. Some or all of the patient data may be transmitted, using a second wireless communication protocol, between the computing device 120 and the display 130. Some or all of the patient data may also be transmitted, using a third wireless communication protocol, from the computing device 120 to the nodes of the telecommunications networks. In some embodiments, the third wireless communication protocol may be different than the first and second wireless communication protocols. For example, the first and second wireless communication protocols may use relatively short-range communication links. In some embodiments, the first and second wireless communication protocols may use a frequency between 2.4 and 2.5 GHz. In some embodiments, the first and second wireless communication protocols may be Bluetooth. In some embodiments, the third wireless communication protocol may be a longer-range communication link. For example, the third wireless communication protocol may be a telecommunications link. Any number or type of telecommunications links may be used (e.g., 5G, 4G, LTE, satellite).

In the downlink direction, audio and video data received from the doctor may be transmitted from the computing device to the display 130. In some embodiments, this data may be carried over the same wireless communication link used to transmit patient data from the computing device to the display 130. In some embodiments, the doctor may also transmit instructions to be received and executed by the medical devices 116. For example, the doctor may wish to power on a device, test whether it is working correctly, perform a measurement, or adjust a testing parameter. Accordingly, information may be received from the doctor by the computing device 120 and transmitted to the medical devices 116. In some embodiments, this information may include instructions, which may then be performed by medical devices. In some embodiments, the information transmitted from the computing device 120 to the medical devices 116 may be transmitted using the same wireless communication link that is used to transmit patient data from the medical devices 116 to the computing device 120.

Figure 2:
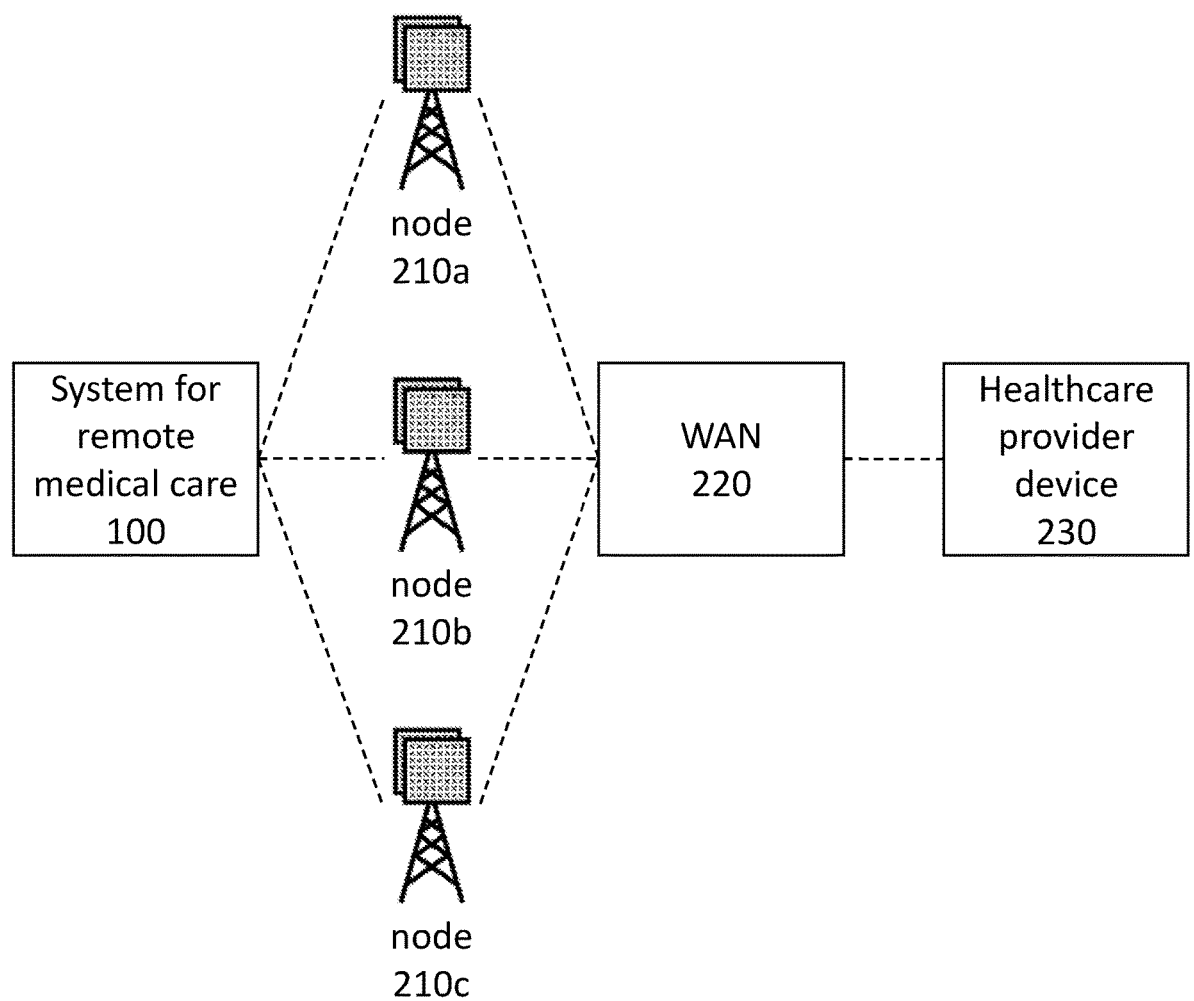
FIG. 2 shows an exemplary network for enabling communication between system 100 and a doctor device 230.

FIG. 2 shows an exemplary network for enabling communication between system 100 and a doctor device 230. In some embodiments, the system 100 may establish communication links with a plurality of network nodes 210*a*, 210*b*, 210*c*. Although three nodes are shown in FIG. 2, the system may establish communication links with any number of nodes. Further, although the nodes 210*a*, 210*b*, 210*c* are depicted as being physically separate (e.g., on separate towers), multiple nodes may be co-located in practice. For example, different network providers may provide nodes at a common location or on a common tower. In such cases, the system 100 may communicate with one or all of these nodes simultaneously. Data may be transmitted from the system to the nodes 210 and then to a WAN 220, such as the internet. The data may then be transmitted from the WAN to a doctor device 230. Optionally, the doctor device may also connect wirelessly to the WAN through one or more telecommunications networks. Data may also be transmitted in the reverse direction, originating at the doctor device 230, passing through the WAN 220 and nodes 210, and to the system 100.

Cellular service is often unreliable in remote areas. To overcome this technical challenge, the system 100 may be enable communications with multiple network nodes simultaneously. This may allow the total bandwidth available to the system 100 to be significantly improved. It may also improve the reliability of the connection, because when one communication link fails, the system can shift communications to links that remain operative.

For example, the computing device 120 may receive patient data, video data, and audio data, directly or indirectly, from the medical devices, cameras, and microphones, respectively. The computing device (or other device such as a display) may generate a plurality of data packets which may include information related to the patient data, the audio data, and the video data. The system may establish, using at least in part the plurality of access credentials, telecommunications links with a plurality of network nodes 210*a*, 210*b*, 210*c*. The system may then transmit, using a first antenna of the plurality of antennas, a first set of data packets of the plurality of data packets to the first node, and it may simultaneously transmit, using a second antenna of the plurality of antennas, a second set of data packets of the plurality of data packets to the second node. Upon detecting an interruption in the link to the first node, the system may transmit a third set of data packets to the second node, where the third set of data packets would have been sent to the first node in the absence of the detected interruption. Communication links may be established with any number of nodes and data may be partitioned into any number of sets to be transmitted to respective nodes. Further, the bandwidth of each link may be measured, and the number of packets transmitted via each link may be adjusted upward or downward based on the quality of the connection. For example, the system may determine that a first communication link has a higher available bandwidth than a second communication link, and it may accordingly assign more packets to be delivered through the first communication link than the second communication link.

Since the system 100 may partition a stream of data into multiple sets to be transmitted through multiple network providers' networks, it may be advantageous to transmit redundant information through multiple of these networks. For example, the system 100 may transmit common information to each network which may then be used to reassemble the transmission to be played at the doctor device 230. The redundant information may be used to detect errors or degradations in service. In some embodiments, the system may determine, based on a detected interruption in a link to one of the network nodes that information was not successfully transmitted due to the interruption. The system may further transmit replacement data packets to a different node, where the replacement data packets include the information that was not successfully transmitted due to the interruption.

Multi-node communications may also be used for downlink transmissions. For example, the system 100 may receive a set of data packets from a first node 210*a* and another set of data packets from a second node 210*b* (and any number of additional nodes). The system may then combine the data from the nodes. In some embodiments, combining the data may yield one or more segments of video or audio data. The system may then play the segment of video or audio data. For example, the computing device 120 may transmit the segment to the display, where it may then be played.

Figure 3:
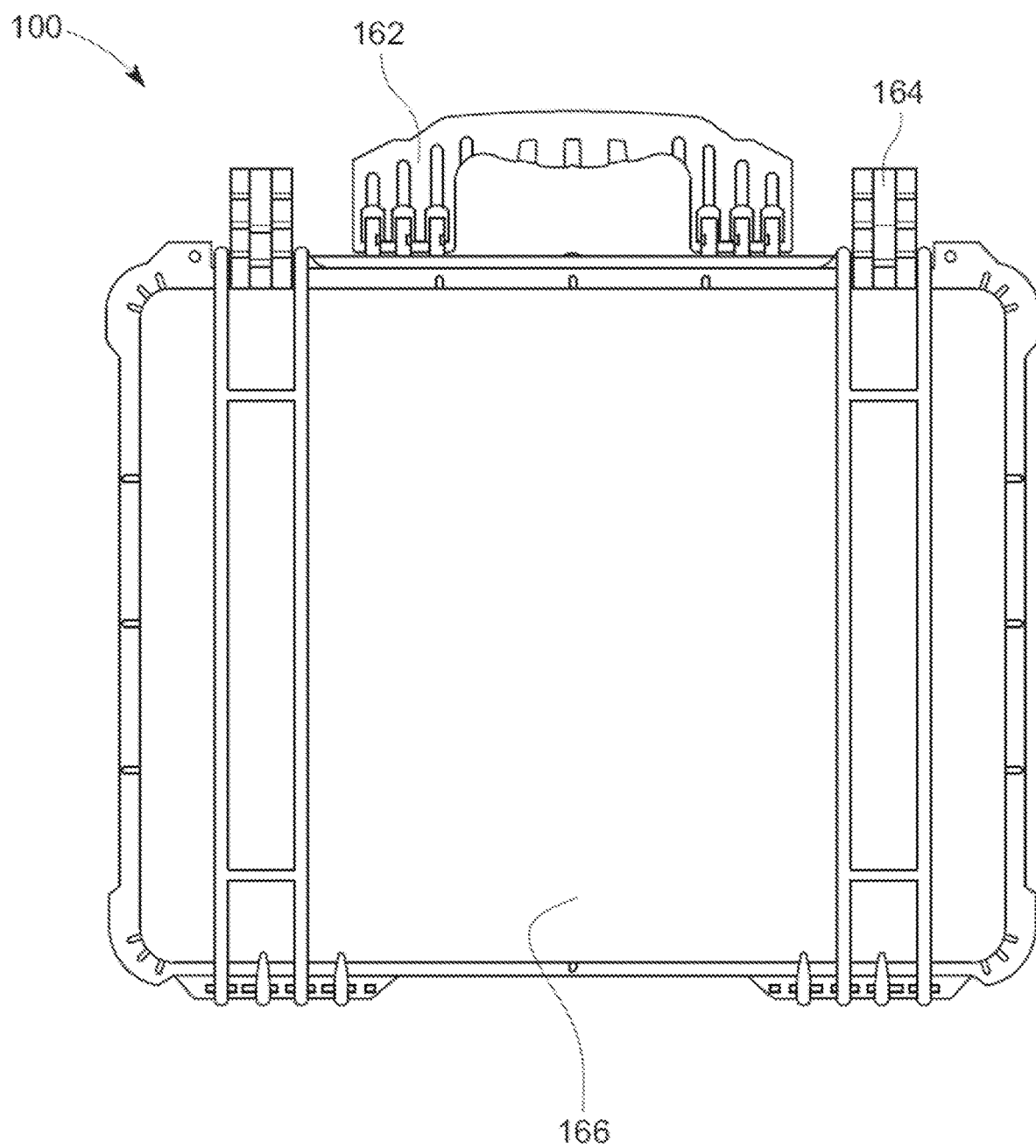
FIG. 3 shows a perspective view of an exemplary system 100 in a closed state.

FIG. 3 shows a perspective view of an exemplary system 100 in a closed state. The system may include a case with a lid 166, a lower portion 168 (see FIGS. 4-5), and a handle. The case may also include one or more latches 164, which may hold the case in a closed position for transport.

Figure 4:
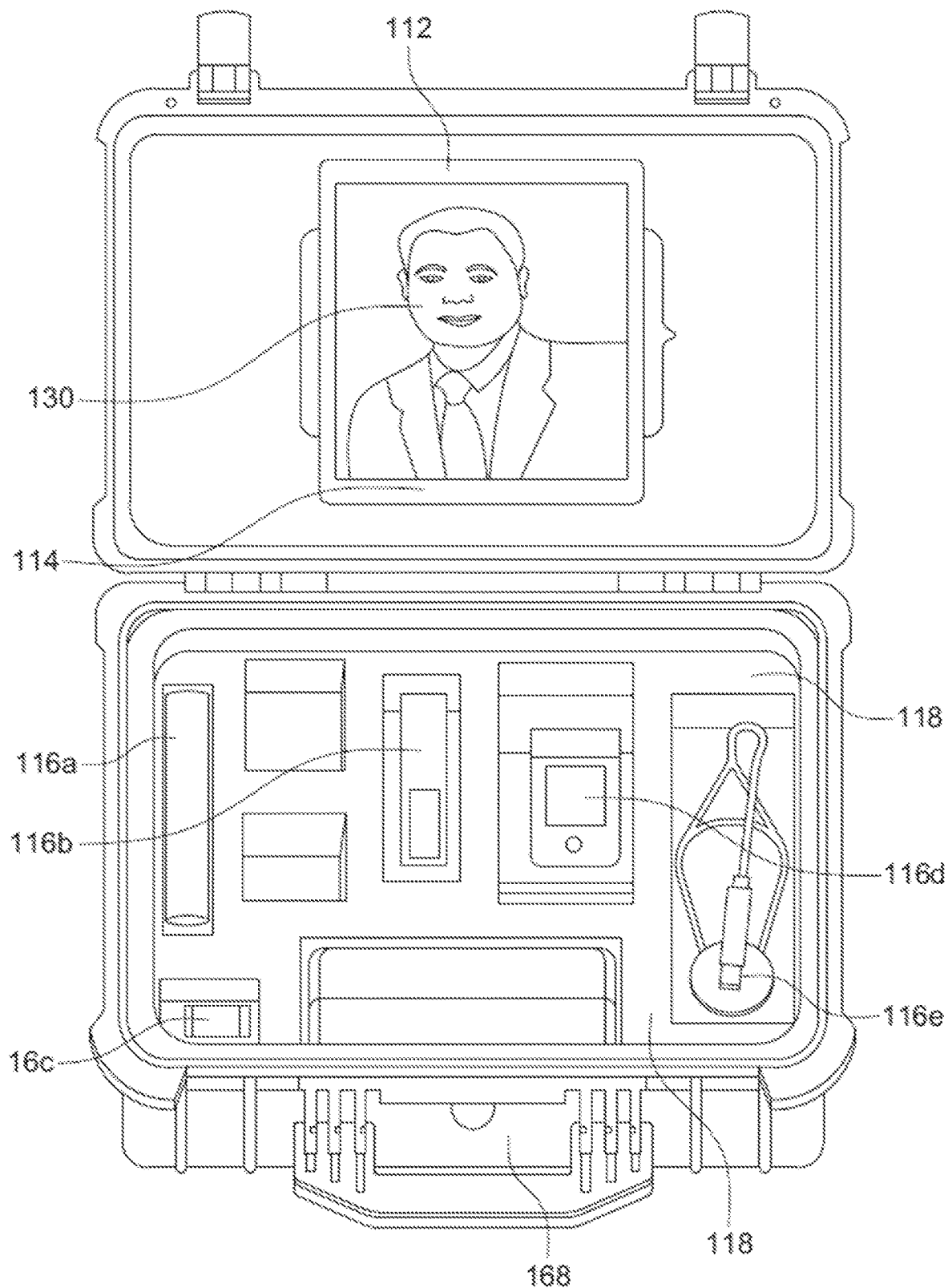
FIG. 4 shows a perspective view of an exemplary system 100 in an open state.

FIG. 4 shows a perspective view of an exemplary system 100 in an open state. In some embodiments, a display 130 may be coupled to the lid 166. The display 130 may optionally be a tablet. In some embodiments, the display 130 may include one or more cameras 112 and one or more microphones 114. In some embodiments, the display 130 may also include one or more speakers. A lower portion 168 of the case may support a tray 118. For example, the lower portion 168 may include a shoulder configured to engage and support a lip of the tray 118. The tray may include a plurality of receptacles. Each receptacle may be configured to receive a respective medical device 116*a*, 116*b*, 116*c*, 116*d*, 116*e*, etc. In some embodiments, the tray may be made from an antimicrobial material (including, but not limited to, materials that include antimicrobial additives). In some embodiments, the antimicrobial material may also be biocompatible. In some embodiments, the case, tray, or other components may also be made from an antimicrobial material. In some embodiments, the antimicrobial material may be antimicrobial polyurethane. In other embodiments, the antimicrobial material may be copper sulfate. Medical care kits have traditionally used foam to support the devices held therein. This has been considered important due to the risk of damage to the devices as the kit is transported. The systems disclosed herein, however, may be intended to be self-administered by a patient after shipping, prompting a need for the surfaces of the system, including the surfaces supporting the medical devices, to resist contamination and be readily disinfected. The use of antimicrobial and easily disinfected materials, such as antimicrobial polyurethane and/or copper sulfate, therefore proceeds contrary to established wisdom, and meets a need that has not previously been recognized for self-administrable medical examination systems. At the same time, the risk of damage to the devices can be mitigated by designing the shape and contours of the compartments to better support the medical devices and absorb shocks, as well as by incorporating magnets or other locking mechanisms to prevent the medical devices from shifting during transportation. In some embodiments, the tray or case may be self-sterilizing, or they may be easily sterilized by wiping with a disinfecting solution or by applying disinfecting energy (e.g., UVC radiation).

Figure 5:
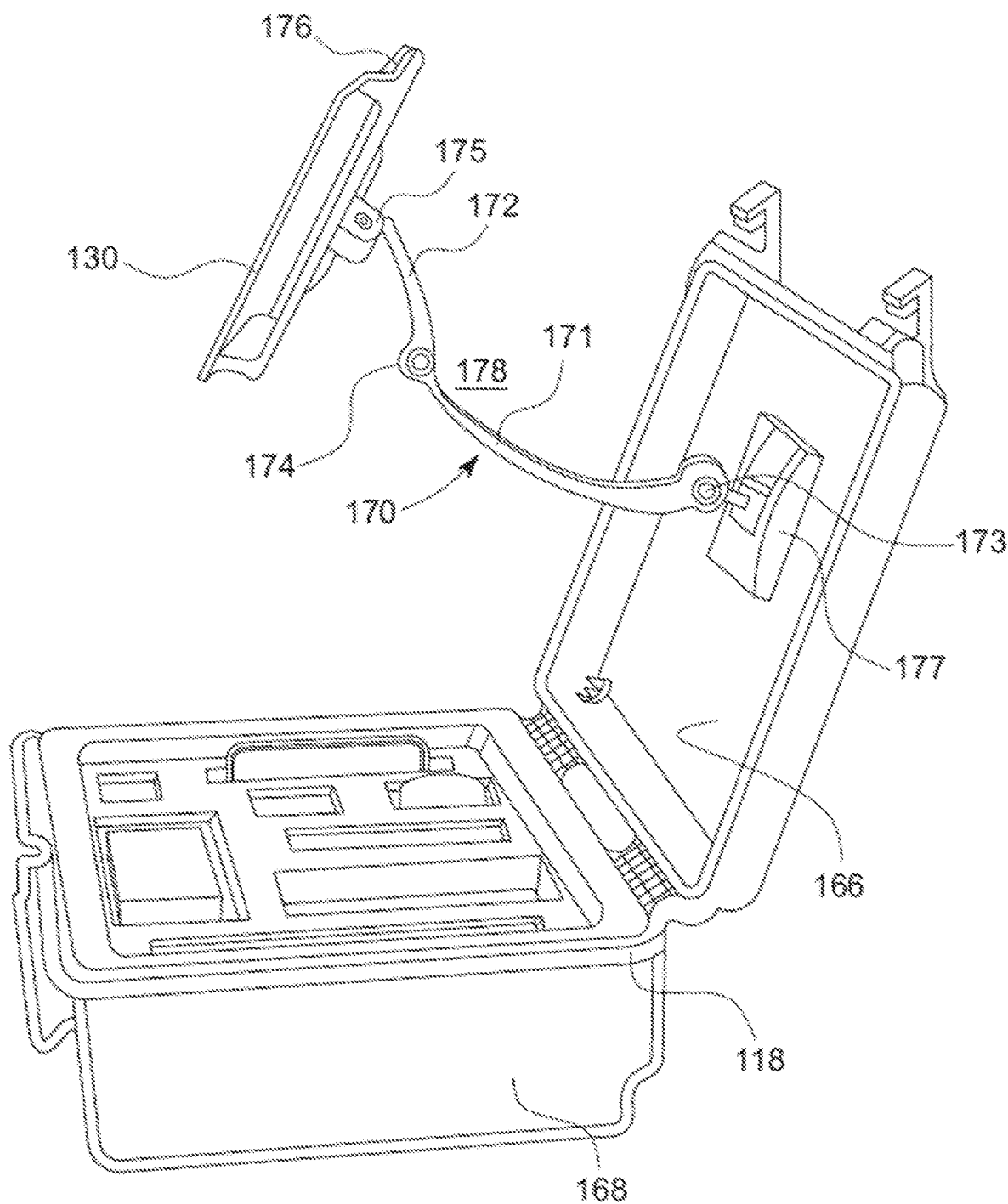
FIG. 5 shows a perspective view of an exemplary system in an open state in which a support arm 170 is extended.

FIG. 5 shows a perspective view of an exemplary system in an open state in which a support arm 170 is extended. In some embodiments, display 130 may be coupled to lid 166 by a support arm 170. In some embodiments, support arm may include multiple segments which may pivot or telescope relative to one another. For example, in the depicted embodiment, support arm 170 includes a first segment 171 and a second segment 172 which are coupled to one another via a pivotable joint 174. The support arm 170 may be coupled to the lid by a joint 173. In some embodiments, joint 173 may enable the arm 170 to move in two or more degrees of freedom. For example, the arm 170 may be pivoted about an axis that is normal to the plane of the lid 166, and it may also be pivoted about an axis that is parallel to the plane of the lid 166. In some embodiments, the display 130 may be attached to the arm 170 by a holding portion 176. The holding portion 176 may be pivotable relative to the arm. For example, the holding portion 176 may be attached to the arm 170 by a pivotable joint 175. In some embodiments, a first camera may be associated with the display 130 (i.e., it may be a component of a display table). A second camera 178 may be separate from the display. In some embodiments, the second camera may be attached to the arm 170 via a coupling that extends directly between the second camera 178 and the arm 170. In some embodiments, the first camera may be arranged to capture video of a patient's face, and the second camera may be arranged to capture video of another portion of the patient. For example, while the first camera captures video of the patient's face, the second camera may capture video of a patient's hands. In some embodiments, one of the cameras may be part of or be replaced with a tracking system that is configured to detect movements of a person's hand or other body part. Hand tracking systems are commercially available, and may be beneficially incorporated into the systems described herein. This arrangement may be particularly advantageous where a doctor wishes to conduct an evaluation where the patient's face and another body part (e.g., hands or written information that the patient records with his or her hands) simultaneously, as may be the case, for example, in a neurocognitive evaluation. In multi-camera embodiments, the cameras may simultaneously transmit information to the computing device 120, which may then transmit the information to a doctor using the processes described above with respect to FIGS. 1 and 2.

Figure 6:
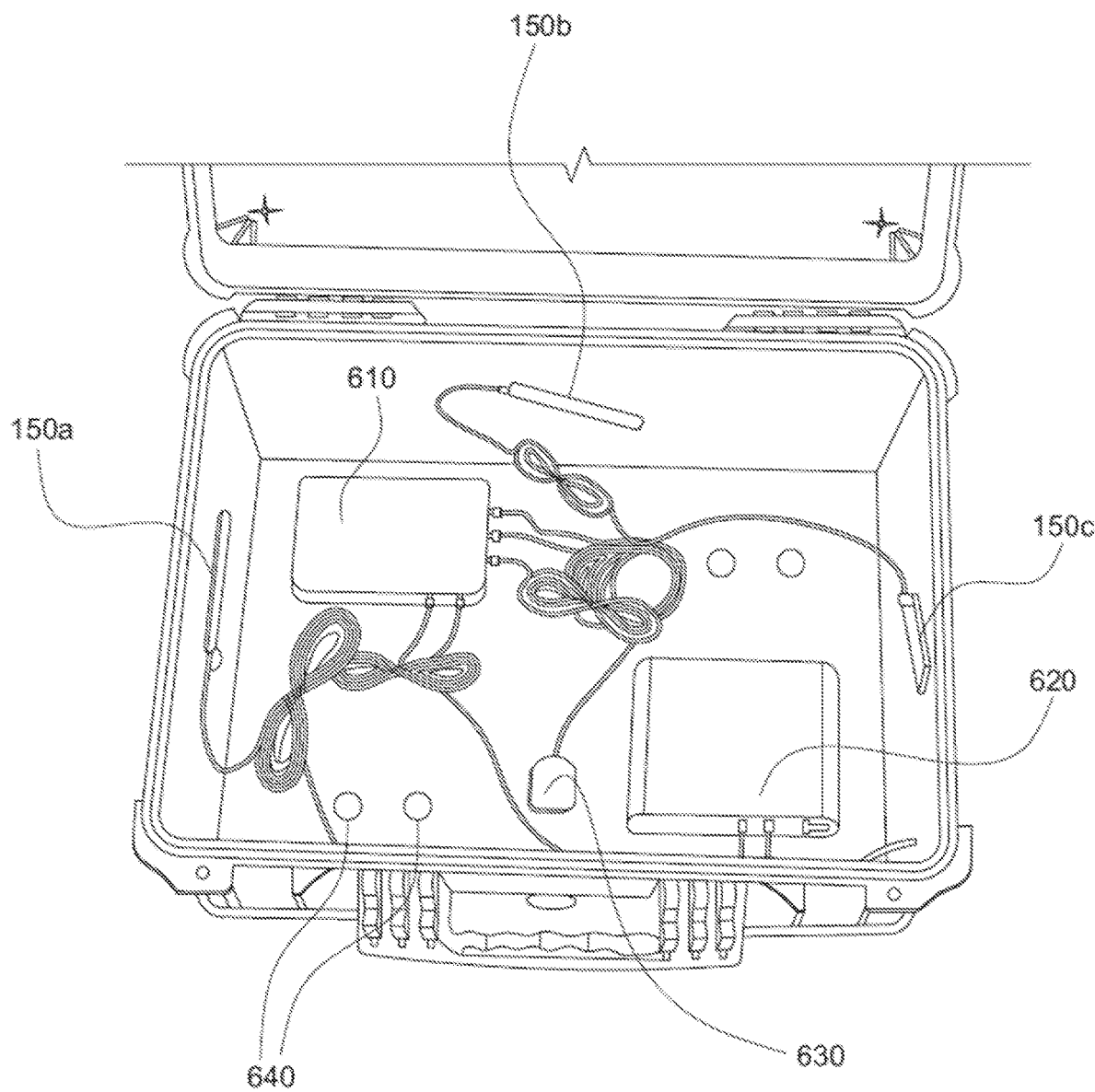
FIG. 6 shows an exemplary illustration of a system 100 in which a tray and medical devices have been removed to show other components.

FIG. 6 shows an exemplary illustration of a system 100 in which a tray and medical devices have been removed to show other components. The system may include one or more routers 610, one or more batteries 620, and a plurality of antennas 150a, 150b, 150c. In some embodiments, the system may include a GPS antenna 630. In some embodiments, the system 100 may act as a WiFi hotspot. In some embodiments, the one or more routers 610 may be configured to transmit and receive signals via antennas 150 to a wide area network, such as the internet. For example, the one or more routers may be configured to communicate via cellular, 5G, 4G, LTE, satellite, sub 6 GHz networks, mmWave, or any other suitable wireless or wired communication technology. In some embodiments, the one or more routers 610 may also be configured to communicate, directly or indirectly, with local devices, such as the medical devices and display within system 100 via local wireless communication technologies, such as WiFi and Bluetooth. In some embodiment, a first set of antennas may be used for cellular communications with network nodes, and a second set of antennas may be used for WiFi communications with local devices (e.g., the medical devices, the display, or other user devices near the system 100). In some embodiments, the antennas may be arranged such that they are angularly offset from one-another. For example, a pair of antennas used for cellular communications may be tilted relative to one-another by an offset angle between 30° and 60°, between 40° and 50°, or most preferably, by 45°. This may advantageously improve the cellular reception of the system by improving the likelihood that at least one of the antennas will be disposed in a suitable orientation to optimize signal strength. In some embodiments, the one or more routers 610 may be separate devices configured to communicate using different wireless communication technologies, or they may be a single device configured to communicate using multiple wireless communication technologies. In some embodiments, a computing device 120 may be or include the one or more routers 610. In some embodiments, the case may include a plurality of mounting structures 640, which may be configured to facilitate the attachment of devices (e.g., routers, computing devices, antennas, batteries) to the case. For example, mounting structures 640 may be threaded holes configured to receive bolts, such that devices may be easily bolted to the case.

In some embodiments, the system 100 may include a modem configured to transmit to nodes of a telecommunication at high power. For example, the system 100 may include a cellular modem configured to transmit at an average power of approximately 1.25 Watts. In other embodiments, the average transmission power may be greater than 0.2 Watts, greater than 0.3 Watts, greater than 0.5 Watts, or greater than 1.0 Watts. The U.S. Federal Communications Commission (FCC) regulates cellular devices and ordinarily limits such devices to a maximum transmission power of 0.2 Watts. Such devices may be referred to as Class 3 FCC devices. Higher-powered devices may be referred to as Class 1 or Class 2 FCC devices. By using a modem capable of transmitting at high power (e.g., 1.25 Watts), service quality can be dramatically improved, and the system 100 can be used in increasingly remote areas. Further, the system 100 may be configured to transmit and receive communications on frequencies reserved for public safety communications. For example, the system may be configured to communicate on Band 14 and/or the First Responder Network Authority (FirstNet). This may also improve service quality and further expand the geographic areas that the system 100 can be used.

Figure 7:
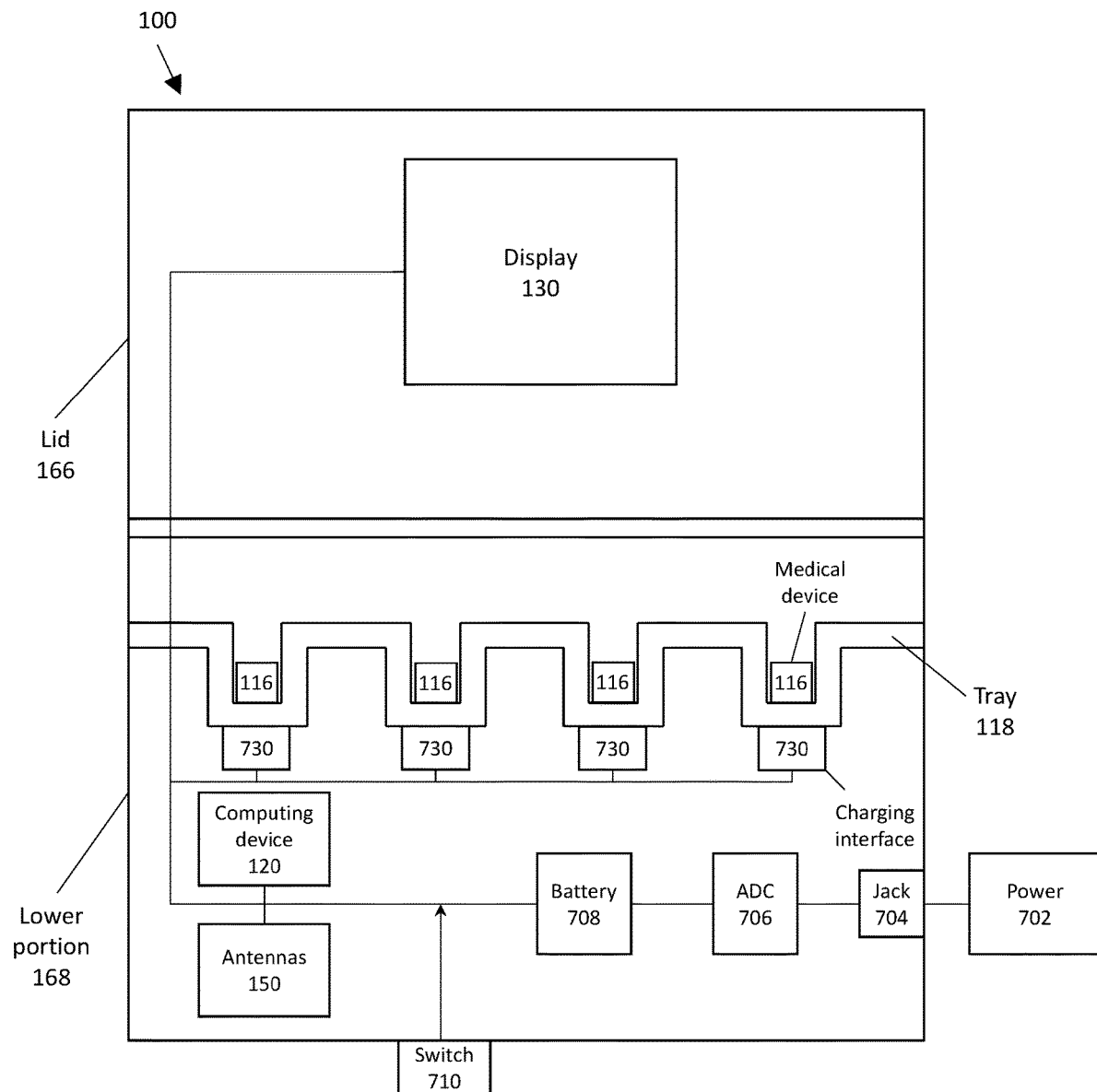
FIGS. 7-9 show exemplary charging embodiments which may be used to supply power to the medical devices 116.
Figure 8:
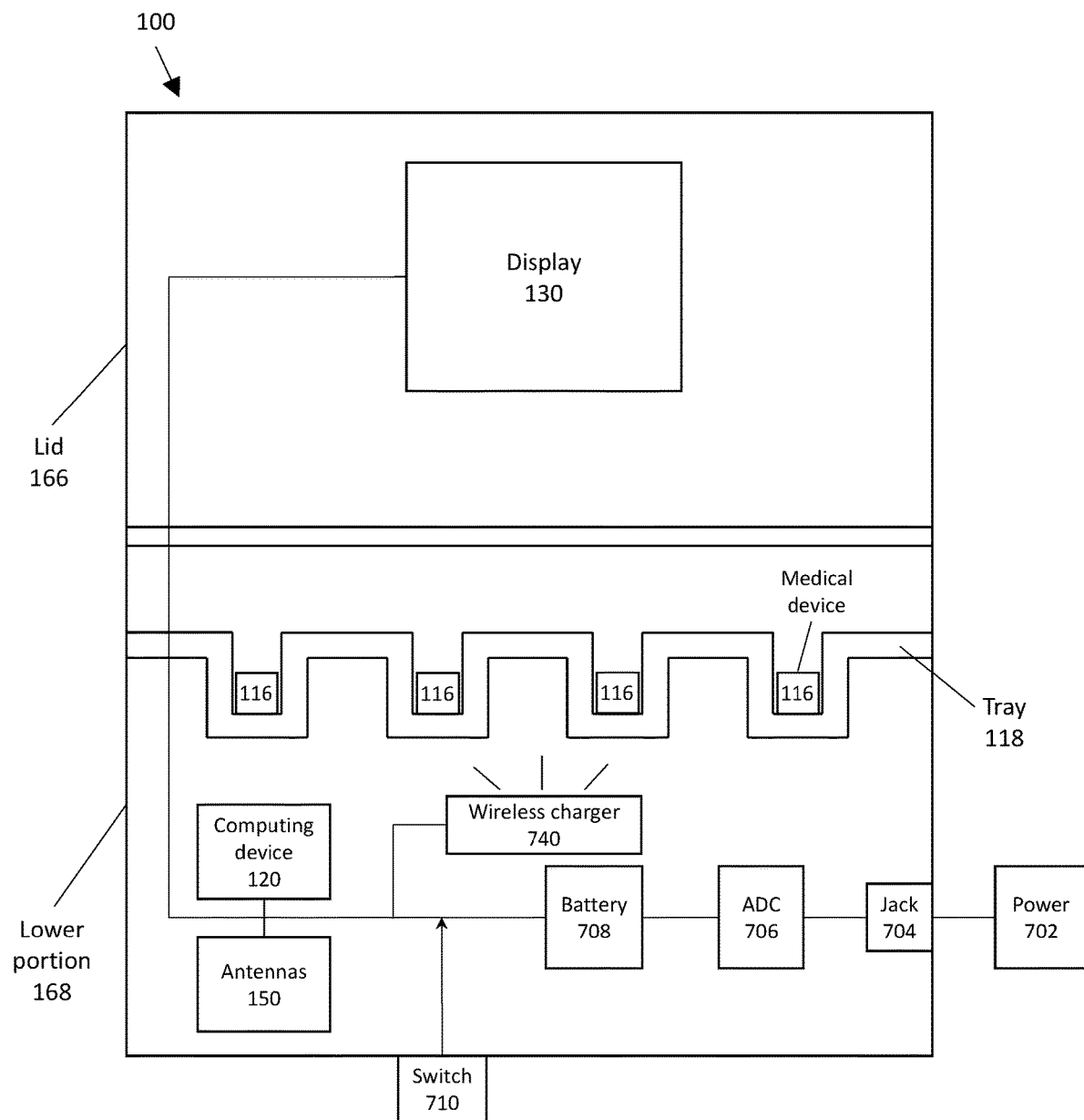
Figure 9:
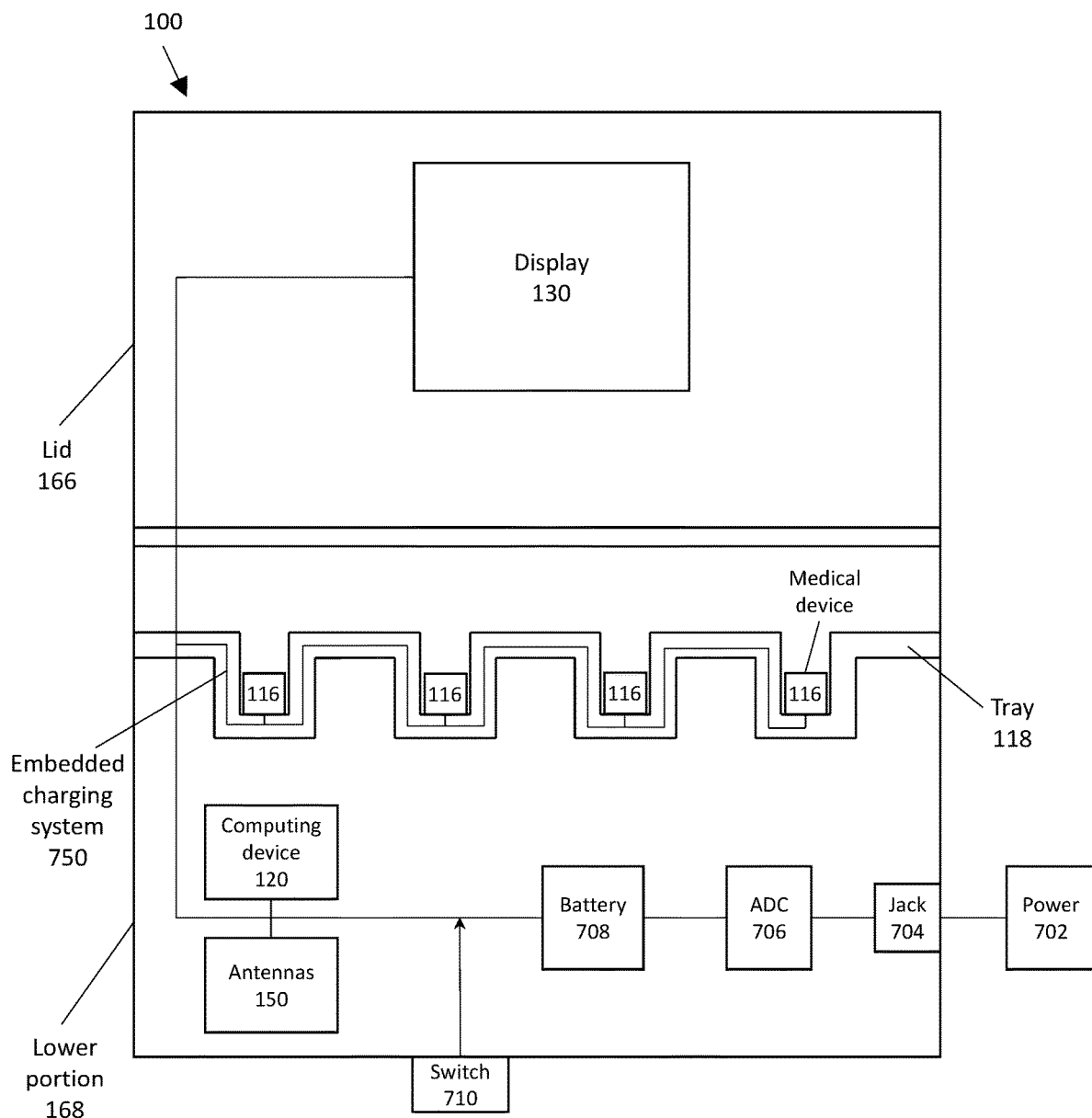

FIGS. 7-9 show exemplary charging embodiments which may be used to supply power to the medical devices 116. These charging embodiments may be included in any of the embodiments described herein with respect to FIGS. 1-6 and 10. As shown in FIG. 7, the system may include a tray 118 which may have a plurality of receptacles. Each receptacle may be configured to receive a respective medical device 116. Power may be supplied to the system 100 by plugging the system into a power outlet 702. The system may have a jack 704, which may be configured to receive a power cable. The system may further include an AC/DC converter 706. In some embodiments, an AC/DC converter may instead be included in a power cable, such that the AC/DC converter may be omitted from the case. The system 100 may further include a battery 708, which may be configured to store energy received from a power outlet 702. The system may include a power switch 710. Optionally, the power switch may power on/off one, some, or all of the computing device 120, display 130, antennas 150, and medical devices 116. Power may be supplied from the battery (or other component such as an AC/DC converter or power cable) to one, some, or all of the computing device 120, display 130, and antennas 150.

Power may also be supplied to a plurality of charging interfaces 730. Charging interfaces may be electrical pads or pins or any other structure that may be configured to deliver power to one or more of the medical devices 116. In some embodiments, inductors may be affixed to one side of the tray such to deliver power across the material of the tray and to the medical devices, which may be configured to be wirelessly charged. In other embodiments, a wire may be passed through the tray so that a wired charging interface may be disposed within the receptacle, such that the charging interface may engage and charge a medical device as it sits in the receptacle. In some embodiments, the receptacles may include magnets which may be arranged to guide the medical devices (which may include corresponding magnets) into a correct position to be charged (e.g., such that charging contacts of the respective medical device engage charging contacts of the respective charging interface 730).

FIG. 8 shows an embodiment that is similar to the embodiment of FIG. 7, except that the wired (or partially wired) charging system of the FIG. 7 embodiment is replaced by a wireless charger 740. In some embodiments, a wireless charger 740 may be coupled to the power supply to transmit power wirelessly to the medical devices 116 as they are disposed in their respective receptacles. In this embodiment, as in the embodiment shown in FIG. 7, magnets may be used to ensure that the medical devices are disposed in an optimal position for charging and transportation. For example, the use of magnets may prevent or reduce the extent to which the medical devices shift during transportation, which may better prevent damage to the medical devices. This can be particularly advantageous where foam cushions are not used to support the medical devices. Avoiding the use of foam cushions may be desired because foam is difficult to disinfect.

FIG. 9 shows an embodiment that is similar to the embodiments of FIGS. 7 and 8, except that the embodiment shown in FIG. 9 has a charging system 750 that is integrated into tray 118. For example, a charging system 750 may be imbedded into tray 118 and coupled to the power source 708 of the system. The imbedded charging system 750 may include conductors which may run through the material of the tray 118 and supply power to charging interfaces in the respective receptacles. Similar to the embodiment of FIG. 7, the charging interfaces may be wired contacts (e.g., pins, plugs) or wireless interfaces (e.g., inductors). The wired (or partially wired) charging system of the FIG. 7 embodiment is replaced by a wireless charger 740. In this embodiment, as in the embodiment shown in FIG. 7, magnets may be used to ensure that the medical devices are disposed in an optimal position for charging.

Any of the embodiments described above with respect to FIGS. 7-9 can be manufactured by molding a case and/or tray from a material having compounds that can be selectively activated by an energy source, such as a laser. The energized portions of the case and/or tray can then be used in a metal deposition process to deposit circuit traces and other electronic components (such as inductors, antennas, and/or power distribution components) directly onto the material of the case and/or tray. For example, metallic or polymeric additives suitable for use in a laser direct structuring (LDS) process may be incorporated into the material used in the case and/or tray. Suitable materials include the TECACOMP® LDS compounds sold by Ensinger. A laser may then be used to form the lines along which conductive traces should be formed, and the case and/or tray may then be subjected to a deposition process (e.g., be placed in an electroless copper bath) to form the desired circuits on the case and/or tray.

Figure 10:
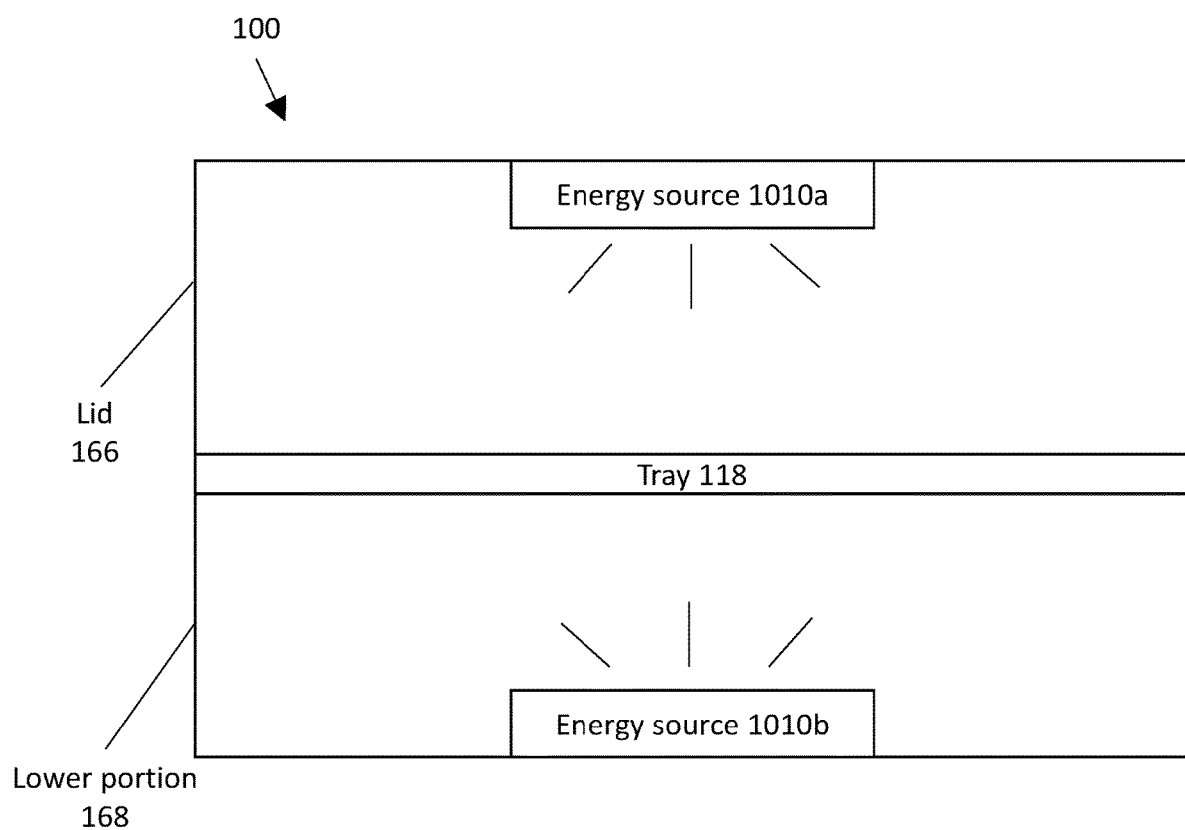
FIG. 10 shows an exemplary system 100 that includes energy sources 1110a, 1110b for sterilizing medical devices 116.

FIG. 10 shows an exemplary system 100 that includes energy sources 1110a, 1110b for sterilizing medical devices 116. As described above with respect to FIGS. 4-9, the system 100 may include a tray 118, which may have a plurality of receptacles for holding medical devices 116. In some embodiments, it may be desirable for the system to enable automatic sterilization of the medical devices 116 before or after they are used. In some embodiments, a first energy source 1010a may be attached to a lid 166 of the case to direct energy at a top surface of the medical devices when the case is in a closed state. In some embodiments, a second energy source 1010b may be attached to a lower portion 168 of the case to direct energy at a lower surface of the medical devices when the case is in a closed state. In some embodiments, the energy sources 1010a, 1010b may be UV radiation sources. In some embodiments, the energy sources 1010a, 1010b may be UVC radiation sources. In some embodiments, the tray 118 may be made in whole or in part of a material that does not block UV or UVC radiation. For example, the tray 118 may be made in whole or in part of quartz, sapphire, or other material that allows UV or UVC radiation to pass. This arrangement may be incorporated in any of the embodiments disclosed herein.

A significant advantage of the systems described herein is that they are well-suited to be self-administered by a patient. Patients may simply open the case and power on the system (which may include, for example, one or more of plugging in the system, powering on one or more of the devices, and completing any log-in prompts), and the system may automatically establish communication links and be ready to conduct a telehealth appointment. For example, upon initiating use of the system by transitioning the case from the closed state to the open state and powering on the system, including one or more of the plurality of medical devices and/or the computing device, the system may be configured to automatically establish a first communication channel between the computing device and at least one of the medical devices of the plurality of medical devices without requiring further action by a user. The first communication channel may be direct or indirect. For example, the medical devices may transmit data to a display, which may then transmit the data to the computing device. The system may be further configured to automatically establish a second communication channel between the computing device and the one or more nodes of the telecommunications network without requiring further action by the user.

Further, by using medical devices that communicate data wirelessly and charge automatically when they are disposed in their receptacles, the system may require essentially no-set up before use or clean-up after use. Likewise, a self-sanitation feature may further reduce set-up and clean-up. An adjustable support arm also facilitates a self-administered telehealth appointment by allowing the patient to easily move the display or camera to an orientation that is suitable to conduct the examination.

These advantages may eliminate (or significantly reduce) the need to have a technician on-site with the patient to conduct the telehealth appointment, thereby significantly reducing the cost and improving the convenience of using the system.

Numbered Embodiments

A1. A telehealth system comprising:
   a case, the case housing at least:
      a display;
      a microphone;
      a camera;
      a plurality of medical devices;
      a plurality of antennas;
      a plurality of access credentials; and
      a computing device comprising a processor;
   wherein the system is configured to:
      obtain, using a first medical device of the plurality of medical devices,
   patient data indicating a health parameter of a patient;
      transmit the patient data to the computing device;
      obtain, using the microphone, audio data;
      obtain, using the camera, video data;
      generate a plurality of data packets, the plurality of data packets collectively comprising information related to the patient data, the audio data, and the video data;
      establish, using at least in part the plurality of access credentials, communications links with a plurality of network nodes, the plurality of nodes comprising a first node and a second node;
      transmit, using a first antenna of the plurality of antennas, a first set of data packets of the plurality of data packets to the first node;
      while transmitting the first set of data packets to the first node using the first antenna, transmit, using a second antenna of the plurality of antennas, a second set of data packets of the plurality of data packets to the second node;
      detect an interruption in the link to the first node;
      as a result of detecting the interruption, transmit a third set of data packets to the second node, wherein the third set of data packets would have been sent to the first node in the absence of the detected interruption.

A2. The system of embodiment A1, wherein the system is further configured to transmit redundant information to both the first node and the second node.

A3. The system of any of embodiments A1-A2, wherein the system is further configured to:
   receive a fourth set of data packets from the first node;
   receive a fifth set of data packets from the second node;
   combine data from the fourth set of data packets and the fifth set of data packets to yield a video segment; and
   play the video segment on the display.

A4. The system of any of embodiments A1-A3, wherein the first node is associated with a first network provider and the second node is associated with a second network provider that is different than the first network provider.

A5. The system of any of embodiments A1-A4, wherein the system is further configured to:
   determine, based on the detected interruption in the link to the first network node, information that was not successfully transmitted due to the interruption; and
   transmit replacement data packets to the second node, the replacement data packets comprising the information that was not successfully transmitted due to the interruption.

A6. The system of any of embodiments A1-A5, wherein the system is configured to transmit the patient data to the computing device using a first wireless communication protocol and the first antenna is configured to transmit the first set of data packets to the first node using a second wireless communication protocol that is different than the first wireless communication protocol.

A7. The system of any of embodiments A1-A6, wherein the computing device is configured to wirelessly receive information from multiple of the plurality of medical devices simultaneously.

A8. The system of any of embodiments A1-A7, wherein the system is further configured to:
   transmit the patient data from one or more of the plurality of medical devices to the display; and
   display, using the display, an indication based on the patient data received from the one or more of the plurality of medical devices.

A9. The system of any of embodiments A1-A8, wherein the display is coupled to a lid of the case by a support arm, the support arm being pivotable relative to the lid to allow a position of the display to be adjusted.

A10. The system of embodiment A9, further comprising a first camera and a second camera, the first camera being associated with the display and configured to capture a patient's face, the second camera being separate from the display and configured to capture a part of the patient other than the face.

A11. The system of any of embodiments A1-A10, wherein the system further comprises:
   a tray having a plurality of receptacles;
   a plurality of charging interfaces, each charging interface being associated with a respective receptacle of the plurality of receptacles such that a respective medical device of the plurality of medical devices, when placed in the respective receptacle, is configured to engage the respective charging interface to be charged.

A12. The system of any of embodiments A1-A10, wherein the system comprises a tray having a plurality of receptacles; and
   a wireless charger, the wireless charger being configured to charge multiple medical devices of the plurality of medical devices when the multiple medical devices are in respective receptacles of the plurality of receptacles.

A13. The system of any of embodiments A1-A10, further comprising a tray made of antimicrobial material.

A14. The system of any of embodiments A1-A10 further comprising:
   a tray comprising a plurality of receptacles, the plurality of medical devices being disposed in respective receptacles of the plurality of receptacles; and
   an ultraviolet light source;
   wherein the tray is disposed between the ultraviolet light source and the medical devices of the plurality of medical devices; and
   the tray comprises a material that transmits ultraviolet light, such that the medical devices are configured to be sterilized by ultraviolet light that is emitted by the ultraviolet light source and passes through the tray.

A15. The system of any of embodiments A1-A14, wherein, upon initiating use of the system by transitioning the case from a closed state to an open state and powering on the system, including one or more of the plurality of medical devices, the system is configured to:
 automatically establish a first communication channel between the computing device and at least one of the medical devices of the plurality of medical devices without requiring further action by a user; and
 automatically establish a second communication channel between the computing device and the one or more nodes of the communications network without requiring further action by the user.

A16. The system of any of embodiments A1-A15, wherein at least one of the first set of data packets and the second set of data packets are transmitted at a power greater than 0.2 Watts.

B1. A telehealth system comprising:
 a case, the case housing at least:
  a display;
  a microphone;
  a camera;
  a plurality of medical devices; and
  a computing device configured to communicate with one or more of the display, the microphone, the camera, and the plurality of medical devices, the computing device being further configured to communicate with one or more nodes of a communications network;
 wherein the display is coupled to a lid of the case by a support arm, the support arm being pivotable relative to the lid to allow a position of the display to be adjusted.

B2. The system of embodiment B1, wherein the support arm comprises a first arm segment and a second arm segment, the first arm segment being coupled to the second arm segment via a hinge.

B3. The system of any of embodiments B1-B2, wherein the system is further configured to:
 transmit, using a first antenna, a first set of data packets to a first network node;
 while transmitting the first set of data packets to the first node using the first antenna, transmit, using a second antenna, a second set of data packets to a second network node;
 detect an interruption in a link to the first network node;
 as a result of detecting the interruption, transmit a third set of data packets to the second node, wherein the third set of data packets would have been sent to the first network node in the absence of the detected interruption.

B4. The system of embodiment B3, wherein the first node is associated with a first network provider and the second node is associated with a second network provider that is different than the first network provider.

B5. The system of any of embodiments B3-B4, wherein the system is further configured to:
 determine, based on the detected interruption in the link to the first network node, information that was not successfully transmitted due to the interruption; and
 transmit replacement data packets to the second node, the replacement data packets comprising the information that was not successfully transmitted due to the interruption.

B6. The system of any of embodiments B1-B5, wherein the computing device is configured to communicate with the plurality of medical devices using a first wireless communication protocol, and the computing device is configured to communicate with the one or more nodes of the communications network using a second wireless communication protocol that is different than the first wireless communication protocol.

B7. The system of any of embodiments B1-B6, wherein the computing device is configured to wirelessly receive information from multiple of the plurality of medical devices simultaneously.

B8. The system of any of embodiments B1-B7, wherein the system is further configured to:
 transmit patient data from a first medical device of the plurality of medical devices to the display; and
 display, using the display, an indication based on the patient data received from the first medical device.

B9. The system of any of embodiments B1-B8, wherein the support arm is coupled to the lid of the case by a hinged joint that enables at least two kinematic degrees of freedom.

B10. The system of any of embodiments B1-B9, further comprising a first camera and a second camera, the first camera being associated with the display and configured to capture a patient's face, the second camera being separate from the display and configured to capture a part of the patient other than the face.

B11. The system of any of embodiments B1-610, wherein the system further comprises:
 a tray having a plurality of receptacles;
 a plurality of charging interfaces, each charging interface being associated with a respective receptacle of the plurality of receptacles such that a respective medical device of the plurality of medical devices, when placed in the respective receptacle, is configured to engage the respective charging interface to be charged.

B12. The system of any of embodiments B1-610, wherein the system comprises a tray having a plurality of receptacles; and
 a wireless charger, the wireless charger being configured to charge multiple medical devices of the plurality of medical devices when the multiple medical devices are in respective receptacles of the plurality of receptacles.

B13. The system of any of embodiments B1-610, further comprising a tray made of antimicrobial material.

B14. The system of any of embodiments B1-610 further comprising:
 a tray comprising a plurality of receptacles, the plurality of medical devices being disposed in respective receptacles of the plurality of receptacles; and
 an ultraviolet light source;
 wherein the tray is disposed between the ultraviolet light source and the medical devices of the plurality of medical devices; and
 the tray comprises a material that transmits ultraviolet light, such that the medical devices are configured to be sterilized by ultraviolet light that is emitted by the ultraviolet light source and passes through the tray.

B15. The system of any of embodiments B1-B14, wherein, upon initiating use of the system by transitioning the case from a closed state to an open state and powering on the system, including one or more of the plurality of medical devices, the system is configured to:
 automatically establish a first communication channel between the computing device and at least one of the medical devices of the plurality of medical devices without requiring further action by a user; and
 automatically establish a second communication channel between the computing device and the one or more nodes of the communications network without requiring further action by the user.

B16. The system of any of embodiments B1-B15, wherein the system is configured to transmit communications to the one or more nodes of the communications at a power greater than 0.2 Watts.

C1. A telehealth system comprising:
a case, the case housing at least:
  a display;
  a microphone;
  a camera;
  a plurality of medical devices;
  a tray comprising a plurality of receptacles shaped and sized to receive respective medical devices of the plurality of medical devices; and
  a computing device configured to communicate with one or more of the display, the microphone, the camera, and the plurality of medical devices, the computing device being further configured to communicate with one or more nodes of a communications network;
wherein the tray is configured to be disinfected by wiping a surface of the tray or by applying UV radiation.

C2. The system of embodiment B1, wherein case comprises a lower portion and a lid, and the tray is supported by a shoulder of the lower portion.

C3. The system of any of embodiments C1-C2, wherein the system is further configured to:
  transmit, using a first antenna, a first set of data packets to a first network node;
  while transmitting the first set of data packets to the first node using the first antenna, transmit, using a second antenna, a second set of data packets to a second network node;
  detect an interruption in a link to the first network node;
  as a result of detecting the interruption, transmit a third set of data packets to the second node, wherein the third set of data packets would have been sent to the first network node in the absence of the detected interruption.

C4. The system of embodiment C3, wherein the first node is associated with a first network provider and the second node is associated with a second network provider that is different than the first network provider.

C5. The system of any of embodiments C3-C4, wherein the system is further configured to:
  determine, based on the detected interruption in the link to the first network node, information that was not successfully transmitted due to the interruption; and
  transmit replacement data packets to the second node, the replacement data packets comprising the information that was not successfully transmitted due to the interruption.

C6. The system of any of embodiments C1-C5, wherein the computing device is configured to communicate with the plurality of medical devices using a first wireless communication protocol, and the computing device is configured to communicate with the one or more nodes of the communications network using a second wireless communication protocol that is different than the first wireless communication protocol.

C7. The system of any of embodiments C1-C6, wherein the computing device is configured to wirelessly receive information from multiple of the plurality of medical devices simultaneously.

C8. The system of any of embodiments C1-C7, wherein the system is further configured to:
  transmit patient data from a first medical device of the plurality of medical devices to the display; and
  display, using the display, an indication based on the patient data received from the first medical device.

C9. The system of any of embodiments C1-C8, wherein the display is coupled to a lid of the case by a support arm, the support arm being pivotable relative to the lid to allow a position of the display to be adjusted.

C10. The system of any of embodiments C1-C9, further comprising a first camera and a second camera, the first camera being associated with the display and configured to capture a patient's face, the second camera being separate from the display and configured to capture a part of the patient other than the face.

C11. The system of any of embodiments C1-C10, wherein the system further comprises:
  a plurality of receptacles disposed in the tray; and
  a plurality of charging interfaces, each charging interface being associated with a respective receptacle of the plurality of receptacles such that a respective medical device of the plurality of medical devices, when placed in the respective receptacle, is configured to engage the respective charging interface to be charged.

C12. The system of any of embodiments C1-C10, wherein the system comprises a plurality of receptacles disposed in the tray; and
  a wireless charger, the wireless charger being configured to charge multiple medical devices of the plurality of medical devices when the multiple medical devices are in respective receptacles of the plurality of receptacles.

C13. The system of any of embodiments C1-C12, wherein the tray is made of antimicrobial material.

C14. The system of any of embodiments C1-C13 further comprising:
  a plurality of receptacles disposed in the tray, the plurality of medical devices being disposed in respective receptacles of the plurality of receptacles; and
  an ultraviolet light source;
  wherein the tray is disposed between the ultraviolet light source and the medical devices of the plurality of medical devices; and
  the tray comprises a material that transmits ultraviolet light, such that the medical devices are configured to be sterilized by ultraviolet light that is emitted by the ultraviolet light source and passes through the tray.

C15. The system of any of embodiments C1-C14, wherein, upon initiating use of the system by transitioning the case from a closed state to an open state and powering on the system, including one or more of the plurality of medical devices, the system is configured to:
  automatically establish a first communication channel between the computing device and at least one of the medical devices of the plurality of medical devices without requiring further action by a user; and
  automatically establish a second communication channel between the computing device and the one or more nodes of the communications network without requiring further action by the user.

C16. The system of any of embodiments C1-C15, wherein the system is configured to transmit communications to the one or more nodes of the communications at a power greater than 0.2 Watts.

D1. A telehealth system comprising:
a case having a closed state and an open state, the case in the closed state housing at least:
  a display;
  a microphone;

a camera;
a plurality of medical devices; and
a computing device configured to communicate with one or more of the display, the microphone, the camera, and the plurality of medical devices, the computing device being further configured to communicate with one or more nodes of a communications network;
wherein, upon initiating use of the system by transitioning the case from the closed state to the open state and powering on the system, including one or more of the plurality of medical devices, the system is configured to:
automatically establish a first communication channel between the computing device and at least one of the medical devices of the plurality of medical devices without requiring further action by a user; and
automatically establish a second communication channel between the computing device and the one or more nodes of the communications network without requiring further action by the user.

D2. The system of embodiment D1, wherein the step of initiating use of the system consists essentially of transitioning the case from the closed state to the open state and powering on the system, including one or more of the plurality of medical devices.

D3. The system of any of embodiments D1-D2, wherein powering on the system comprises plugging in a power cable.

D4. The system of any of embodiments D1-D3, wherein the system is further configured to:
transmit, using a first antenna, a first set of data packets to a first network node;
while transmitting the first set of data packets to the first node using the first antenna, transmit, using a second antenna, a second set of data packets to a second network node;
detect an interruption in a link to the first network node; and
as a result of detecting the interruption, transmit a third set of data packets to the second node, wherein the third set of data packets would have been sent to the first network node in the absence of the detected interruption.

D5. The system of embodiment D4, wherein the first node is associated with a first network provider and the second node is associated with a second network provider that is different than the first network provider.

D6. The system of any of embodiments D4-D5, wherein the system is further configured to:
determine, based on the detected interruption in the link to the first network node, information that was not successfully transmitted due to the interruption;
transmit replacement data packets to the second node, the replacement data packets comprising the information that was not successfully transmitted due to the interruption.

D7. The system of any of embodiments D1-D6, wherein the computing device is configured to communicate with the plurality of medical devices using a first wireless communication protocol, and the computing device is configured to communicate with the one or more nodes of the communications network using a second wireless communication protocol that is different than the first wireless communication protocol.

D8. The system of any of embodiments D1-D7, wherein the computing device is configured to wirelessly receive information from multiple of the plurality of medical devices simultaneously.

D9. The system of any of embodiments D1-D8, wherein the system is further configured to:
transmit patient data from a first medical device of the plurality of medical devices to the display; and
display, using the display, an indication based on the patient data received from the first medical device.

D10. The system of any of embodiments D1-D9, wherein the display is coupled to a lid of the case by a support arm, the support arm being pivotable relative to the lid to allow a position of the display to be adjusted.

D11. The system of any of embodiments D1-D10, further comprising a first camera and a second camera, the first camera being associated with the display and configured to capture a patient's face, the second camera being separate from the display and configured to capture a part of the patient other than the face.

D12. The system of any of embodiments D1-D11, wherein the system further comprises:
a tray having a plurality of receptacles; and
a plurality of charging interfaces, each charging interface being associated with a respective receptacle of the plurality of receptacles such that a respective medical device of the plurality of medical devices, when placed in the respective receptacle, is configured to engage the respective charging interface to be charged.

D13. The system of any of embodiments D1-D12, wherein the system comprises a tray having a plurality of receptacles; and
a wireless charger, the wireless charger being configured to charge multiple medical devices of the plurality of medical devices when the multiple medical devices are in respective receptacles of the plurality of receptacles.

D14. The system of any of embodiments D1-D12, further comprising a tray made of antimicrobial material.

D15. The system of any of embodiments D1-D12 further comprising:
a tray comprising a plurality of receptacles, the plurality of medical devices being disposed in respective receptacles of the plurality of receptacles; and
an ultraviolet light source;
wherein the tray is disposed between the ultraviolet light source and the medical devices of the plurality of medical devices; and
the tray comprises a material that transmits ultraviolet light, such that the medical devices are configured to be sterilized by ultraviolet light that is emitted by the ultraviolet light source and passes through the tray.

D16. The system of any of embodiments D1-D15, wherein the system is configured to transmit communications to the one or more nodes of the communications at a power greater than 0.2 Watts.

E1. A telehealth system comprising:
a case, the case housing at least:
a display;
a microphone;
a camera;
a plurality of medical devices; and
a computing device configured to communicate with one or more of the display, the microphone, the camera, and the plurality of medical devices, the computing device being further configured to communicate with one or more nodes of a communications network;

wherein the system is configured to:
obtain, using a first medical device of the plurality of medical devices, patient data indicating a health parameter of a patient;
transmit, using a first wireless communication protocol, the patient data from the first medical device to the display;
transmit, using a second wireless communication protocol, the patient data from the display to the computing device;
display, using the display, information related to the patient data;
transmit, using a third wireless communication protocol, the patient data from the computing device to one or more nodes of a communications network, the third wireless communication protocol being different than both the first and second wireless communication protocols.

E2. The system of embodiment E1, wherein the microphone and camera are components of the display, and the display is configured to wirelessly transmit data captured by the microphone or the camera to the computing device.

E3. The system of any of embodiments E1-E2, wherein system is further configured to:
receive, at the computing device, video data from the one or more nodes of the communications network;
transmit the video data from the computing device to the display; and
display, using the display, a video segment based on the video data.

E4. The system of any of embodiments E1-E3, wherein the system is further configured to:
transmit, using a first antenna, a first set of data packets to a first network node;
while transmitting the first set of data packets to the first node using the first antenna, transmit, using a second antenna, a second set of data packets to a second network node;
detect an interruption in a link to the first network node;
as a result of detecting the interruption, transmit a third set of data packets to the second node, wherein the third set of data packets would have been sent to the first network node in the absence of the detected interruption.

E5. The system of embodiment E4, wherein the first node is associated with a first network provider and the second node is associated with a second network provider that is different than the first network provider.

E6. The system of any of embodiments E4-E5, wherein the system is further configured to:
determine, based on the detected interruption in the link to the first network node, information that was not successfully transmitted due to the interruption; and
transmit replacement data packets to the second node, the replacement data packets comprising the information that was not successfully transmitted due to the interruption.

E7. The system of any of embodiments E1-E6, wherein the first wireless communication is the same as the second wireless communication protocol, and both the first wireless communication protocol and the second wireless communication protocol use a frequency between 2.4 and 2.5 GHz.

E8. The system of any of embodiments E1-E7, wherein the computing device is configured to wirelessly receive information from multiple of the plurality of medical devices simultaneously.

E9. The system of any of embodiments E1-E8, wherein the display is coupled to a lid of the case by a support arm, the support arm being pivotable relative to the lid to allow a position of the display to be adjusted.

E10. The system of any of embodiments E1-E9, further comprising a first camera and a second camera, the first camera being associated with the display and configured to capture a patient's face, the second camera being separate from the display and configured to capture a part of the patient other than the face.

E11. The system of any of embodiments E1-E10, wherein the system further comprises:
a tray having a plurality of receptacles;
a plurality of charging interfaces, each charging interface being associated with a respective receptacle of the plurality of receptacles such that a respective medical device of the plurality of medical devices, when placed in the respective receptacle, is configured to engage the respective charging interface to be charged.

E12. The system of any of embodiments E1-E10, wherein the system comprises a tray having a plurality of receptacles; and
a wireless charger, the wireless charger being configured to charge multiple medical devices of the plurality of medical devices when the multiple medical devices are in respective receptacles of the plurality of receptacles.

E13. The system of any of embodiments E1-E10, further comprising a tray made of antimicrobial material.

E14. The system of any of embodiments E1-E10 further comprising:
a tray comprising a plurality of receptacles, the plurality of medical devices being disposed in respective receptacles of the plurality of receptacles; and
an ultraviolet light source;
wherein the tray is disposed between the ultraviolet light source and the medical devices of the plurality of medical devices; and
the tray comprises a material that transmits ultraviolet light, such that the medical devices are configured to be sterilized by ultraviolet light that is emitted by the ultraviolet light source and passes through the tray.

E15. The system of any of embodiments E1-E14, wherein, upon initiating use of the system by transitioning the case from a closed state to an open state and powering on the system, including one or more of the plurality of medical devices, the system is configured to:
automatically establish a first communication channel between the computing device and at least one of the medical devices of the plurality of medical devices without requiring further action by a user; and
automatically establish a second communication channel between the computing device and the one or more nodes of the communications network without requiring further action by the user.

E16. The system of any of embodiments E1-E15, wherein the system is configured to transmit communications to the one or more nodes of the communications at a power greater than 0.2 Watts.

F1. A telehealth system comprising:
a case, the case housing at least:
a display;
a microphone;
a first camera;
a second camera;
a plurality of medical devices; and
a computing device configured to communicate with one or more of the display, the microphone, the first camera, the second camera, and the plurality of medical devices, the computing device being further configured to communicate with one or more nodes of a communications network;

wherein the system, in a deployed state, is configured to:
obtain, using the first camera, first video data of a patient's face;
obtain, using the second camera, second video data of a patient's hand;
transmit, using a wireless communication protocol, the first video data and
the second video data to one or more nodes of a communications network.

F2. The system of embodiment F1, wherein the first camera is associated with the display, and the second camera is separate from the display.

F3. The system of any of embodiments F1-F2, wherein the system is further configured to:
transmit, using a first antenna, a first set of data packets to a first network node;
while transmitting the first set of data packets to the first node using the first antenna, transmit, using a second antenna, a second set of data packets to a second network node;
detect an interruption in a link to the first network node;
as a result of detecting the interruption, transmit a third set of data packets to the second node, wherein the third set of data packets would have been sent to the first network node in the absence of the detected interruption.

F4. The system of embodiment F3, wherein the first node is associated with a first network provider and the second node is associated with a second network provider that is different than the first network provider.

F5. The system of any of embodiments F3-F4, wherein the system is further configured to:
determine, based on the detected interruption in the link to the first network node, information that was not successfully transmitted due to the interruption; and
transmit replacement data packets to the second node, the replacement data packets comprising the information that was not successfully transmitted due to the interruption.

F6. The system of any of embodiments F1-F5, wherein the computing device is configured to communicate with the plurality of medical devices using a first wireless communication protocol, and the computing device is configured to communicate with the one or more nodes of the communications network using a second wireless communication protocol that is different than the first wireless communication protocol.

F7. The system of any of embodiments F1-F6, wherein the computing device is configured to wirelessly receive information from multiple of the plurality of medical devices simultaneously.

F8. The system of any of embodiments F1-F7, wherein the system is further configured to:
transmit patient data from a first medical device of the plurality of medical devices to the display; and
display, using the display, an indication based on the patient data received from the first medical device.

F9. The system of any of embodiments F1-F8, wherein the display is coupled to a lid of the case by a support arm, the support arm being pivotable relative to the lid to allow a position of the display to be adjusted.

F10. The system of any of embodiments F1-F9, wherein the first camera is coupled to the support arm via the display and the second camera is coupled to the support arm via a coupling extending directly between the support arm and the second camera.

F11. The system of any of embodiments F1-F10, wherein the system further comprises:
a tray having a plurality of receptacles; and
a plurality of charging interfaces, each charging interface being associated with a respective receptacle of the plurality of receptacles such that a respective medical device of the plurality of medical devices, when placed in the respective receptacle, is configured to engage the respective charging interface to be charged.

F12. The system of any of embodiments F1-F10, wherein the system comprises a tray having a plurality of receptacles; and
a wireless charger, the wireless charger being configured to charge multiple medical devices of the plurality of medical devices when the multiple medical devices are in respective receptacles of the plurality of receptacles.

F13. The system of any of embodiments F1-F10, further comprising a tray made of antimicrobial material.

F14. The system of any of embodiments F1-F10 further comprising:
a tray comprising a plurality of receptacles, the plurality of medical devices being disposed in respective receptacles of the plurality of receptacles; and
an ultraviolet light source;
wherein the tray is disposed between the ultraviolet light source and the medical devices of the plurality of medical devices; and
the tray comprises a material that transmits ultraviolet light, such that the medical devices are configured to be sterilized by ultraviolet light that is emitted by the ultraviolet light source and passes through the tray.

F15. The system of any of embodiments F1-F14, wherein, upon initiating use of the system by transitioning the case from a closed state to an open state and powering on the system, including one or more of the plurality of medical devices, the system is configured to:
automatically establish a first communication channel between the computing device and at least one of the medical devices of the plurality of medical devices without requiring further action by a user; and
automatically establish a second communication channel between the computing device and the one or more nodes of the communications network without requiring further action by the user.

F16. The system of any of embodiments F1-F15, wherein the system is configured to transmit communications to the one or more nodes of the communications at a power greater than 0.2 Watts.

G1. A telehealth system comprising:
a case, the case housing at least:
a display;
a microphone;
a camera;
a plurality of medical devices;
a tray having a plurality of receptacles, the tray being made of an antimicrobial material; and
a computing device configured to communicate with one or more of the display, the microphone, the camera, and the plurality of medical devices, the computing device being further configured to communicate with one or more nodes of a communications network.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A telehealth system comprising:
a case, the case housing at least:
a display;
a microphone;
a camera;
a plurality of medical devices; and
a computing device configured to communicate with one or more of the display, the microphone, the camera, and the plurality of medical devices, the computing device being further configured to communicate with one or more nodes of a communications network;
wherein the display is coupled to a lid of the case by a support arm, the support arm being pivotable relative to the lid to allow a position of the display to be adjusted;
wherein, upon initiating use of the telehealth system by transitioning the case from a closed state to an open state and powering on the telehealth system, including one or more of the plurality of medical devices, the telehealth system is configured to:
automatically establish a first communication channel between the computing device and at least one of the medical devices of the plurality of medical devices without requiring further action by a user; and
automatically establish a second communication channel between the computing device and the one or more nodes of the communications network without requiring further action by the user.

2. The telehealth system of claim 1, wherein the support arm comprises one or more grippers disposed on opposed sides of the display, the one or more grippers being configured to releasably engage the display.

3. The telehealth system of claim 1, wherein the support arm is coupled to the lid of the case at a joint, and the display is rotatable relative to the joint while the display is engaged by the support arm, and the support arm is rotatable about a first axis that is normal to a plane of the lid and at least a portion of the support arm can be moved about a second axis that is different than the first axis.

4. The telehealth system of claim 1, wherein the telehealth system is further configured to:
transmit, using a first antenna, a first set of data packets to a first network node;
while transmitting the first set of data packets to the first network node using the first antenna, transmit, using a second antenna, a second set of data packets to a second network node;
detect an interruption in a link to the first network node;
as a result of detecting the interruption, transmit a third set of data packets to the second network node, wherein the third set of data packets would have been sent to the first network node in an absence of the detected interruption.

5. The telehealth system of claim 4, wherein the telehealth system is further configured to:
receive a fourth set of data packets from the first network node;
receive a fifth set of data packets from the second network node;
combine data from the fourth set of data packets and the fifth set of data packets to yield a video segment; and
play the video segment on the display.

6. The telehealth system of claim 4, wherein the first network node is associated with a first network provider and the second network node is associated with a second network provider that is different than the first network provider.

7. The telehealth system of claim 4, wherein the telehealth system is further configured to:
determine, based on the detected interruption in the link to the first network node, information that was not successfully transmitted due to the interruption; and
transmit replacement data packets to the second network node, the replacement data packets comprising the information that was not successfully transmitted due to the interruption.

8. The telehealth system of claim 1, wherein the computing device is configured to communicate with the plurality of medical devices using a first wireless communication protocol, and the computing device is configured to communicate with the one or more nodes of the communications network using a second wireless communication protocol that is different than the first wireless communication protocol.

9. The telehealth system of claim 1, wherein the computing device is configured to wirelessly receive information from multiple of the plurality of medical devices simultaneously.

10. The telehealth system of claim 1, wherein the telehealth system is further configured to:
transmit patient data from a first medical device of the plurality of medical devices to the display; and
display, using the display, an indication based on the patient data received from the first medical device.

11. The telehealth system of claim 1, wherein the support arm is coupled to the lid of the case by a hinged joint that enables at least two kinematic degrees of freedom.

12. The telehealth system of claim 1, further comprising a first camera and a second camera, the first camera being associated with the display and configured to capture a face of a patient, the second camera being separate from the display and configured to capture a part of the patient other than the face.

13. The telehealth system of claim 1, wherein the telehealth system further comprises:
a tray having a plurality of receptacles;
a plurality of charging interfaces, each charging interface being associated with a respective receptacle of the plurality of receptacles such that a respective medical device of the plurality of medical devices, when placed in the respective receptacle, is configured to engage the respective charging interface to be charged.

14. The telehealth system of claim 1, wherein the telehealth system comprises a tray having a plurality of receptacles; and
a wireless charger, the wireless charger being configured to charge multiple medical devices of the plurality of medical devices when the multiple medical devices are in respective receptacles of the plurality of receptacles.

15. The telehealth system of claim 1, further comprising a tray made of antimicrobial material.

16. The telehealth system of claim 1, further comprising:
- a tray comprising a plurality of receptacles, the plurality of medical devices being disposed in respective receptacles of the plurality of receptacles; and
- an ultraviolet light source;
- wherein the tray is disposed between the ultraviolet light source and the medical devices of the plurality of medical devices; and
- the tray comprises a material that transmits ultraviolet light, such that the medical devices are configured to be sterilized by ultraviolet light that is emitted by the ultraviolet light source and passes through the tray.

17. The telehealth system of claim 1, wherein the telehealth system is configured to transmit communications to the one or more nodes of the communications at a power greater than 0.2 Watts.

18. The telehealth system of claim 1, wherein the telehealth system further comprises a wireless charger, the wireless charger being configured to transmit energy toward the display.

19. The telehealth system of claim 1, wherein the support arm includes multiple segments that telescope relative to one another.

* * * * *